United States Patent [19]

Packard et al.

[11] Patent Number: 4,851,069
[45] Date of Patent: Jul. 25, 1989

[54] PROCESS FOR MAKING TISSUE-ABSORBENT PARTICLE LAMINATES

[75] Inventors: Thomas D. Packard, Stoughton; William C. Goodchild, Attleboro, both of Mass.

[73] Assignee: Bird Machine Company, Inc., South Walpole, Mass.

[21] Appl. No.: 622,640

[22] Filed: Jun. 20, 1984

[51] Int. Cl.[4] .............................................. B32B 31/00
[52] U.S. Cl. ...................... 156/284; 156/64; 156/83; 156/276; 156/283; 156/308.8; 156/324; 156/324.4; 428/326; 428/327; 604/364; 604/375
[58] Field of Search .................... 156/64, 283, 83, 284, 156/276, 324, 308.8, 324.4; 428/326, 327; 604/364, 375

[56] References Cited

U.S. PATENT DOCUMENTS

| | | | |
|---|---|---|---|
| 2,988,641 | 6/1961 | Gough | 156/64 |
| 3,070,095 | 12/1962 | Torr | 604/364 |
| 3,073,736 | 1/1963 | Lange | 156/182 |
| 3,098,780 | 7/1963 | Krause | 156/64 |
| 3,256,138 | 6/1966 | Welch et al. | 428/327 |
| 4,055,180 | 10/1977 | Karami | 128/287 |
| 4,260,443 | 4/1981 | Lindsay et al. | 156/220 |
| 4,296,234 | 10/1981 | Mindt et al. | 604/375 |

FOREIGN PATENT DOCUMENTS 0080382 6/1983 European Pat. Off. .

OTHER PUBLICATIONS

Reprint of article from "Index 78 Programme, Session 3: Hygiene Absorbent Products" of Paper 4 -Super-Absorbent Polymers for use with Body Exudates, by Schlauch et al., published prior to Jun. 20, 1984.
Process of making Absorbent Laminates Practiced Commercially by (Assignee, Bird Machine Company, Inc.) of South Walpole, Mass., prior to Jun. 20, 1983.

Primary Examiner—John J. Gallagher

[57] ABSTRACT

A process of making a liquid absorbing laminated structure comprising long lengths of absorptive tissues and an intermediate layer of absorptive particles is performed while the tissues are traveling in the direction of their lengths. A film of moistening liquid is transferred to a surface of a first tissue which is then supported in substantially horizontal position and showered with dry absorbent particles, which are rendered adhesive by absorption of the moistening liquid. A second tissue is superposed and the assembly is bonded together by passing it through the nip between a heated roller having a surface temperature of at least 110° C. and a pressure roller. These rollers are pressed together at the nip by a pressure of at least 350 pounds per square inch and each has a surface hardness in excess of 90 Shore A Durometer.

7 Claims, 2 Drawing Sheets

PROCESS FOR MAKING TISSUE-ABSORBENT PARTICLE LAMINATES

BACKGROUND OF THE INVENTION

1. Field of the Invention

The invention relates to a process for making laminates of liquid absorbent tissues with an intervening layer of particulate material of high liquid absorbency. Particularly, the invention concerns such a process suitable for use with long length tissues traveling in the direction of their length at speeds in excess of 200 linear feet per minute.

2. Background Information

In the manufacture of absorbent materials, particularly those for use in absorbing body fluids, it has become generally recognized as desirable to incorporate in the absorbent tissues usually employed particulate material of higher absorbency to bulk ratios than the tissues, thus increasing the absorbency to bulk ratios of the product. Numerous granular or powder absorbents are available for the purpose, such as set forth in European Patent Publication No. 0080382, published June 1, 1983. Of these, the so-called "super absorbent" particles are particularly desirable because of their high absorbency.

Various processes have been proposed for incorporating such particulate material into absorbent tissue products. In the aforesaid European Patent Publication they are introduced into a stream of melt blown polymeric microfibres which is then formed into a web in which the absorbent particles are distributed and held by adhesion of the fibers to the particles. This requires special manufacture of a particular type of absorbent web.

Other processes utilize conventional prefabricated absorbent tissues with an intermediate layer of absorbent particles. In one such process, disclosed in U.S. Pat. No. 4,260,443, the particle layer is deposited on a dry substrate tissue, an overlay tissue is applied, the assembly is embossed to provide separated raised areas, and the overlay tissue in these raised areas is then moistened with water applied by a roller rotating in the direction of travel of the assembly which wets the particles in the raised areas sufficiently to make them tacky and adhesively bond together the tissues and intermediate particle layer in these areas. The product of this process is spot bonded only and likely to delaminate in subsequent handling and use. The absorbent particles, being loose between bonded areas, are free to migrate and bunch to an undesirable extent. Manufacturing problems include the difficulty of embossing absorbent tissues without rupturing them and the lack of applied heat and pressure after moistening, which our experience indicates would be necessary to durability of the spot bonds.

Another prior process making use of the inherent tackiness of the absorbent particles when slightly moistened was practiced commercially by applicants' assignee. In this process, the absorbent particles were mixed with a small amount of moistening agent (a polyhydric alcohol) before being applied as a layer to a base tissue. An overlay tissue was applied over the layer and the assembly was subjected to heat and pressure to set the bonds of the particles to the tissues, the particles having been rendered tacky by the moistening liquid, and thus bind the assembly together. The product of this process proved commercially acceptable, being of high absorbency and low bulk, with the tissues and particles adequately bonded together. However, manufacturing difficulties were experienced, due mainly to the fact that the absorbent particles were rendered tacky by moistening before they were applied to the base tissue. This caused the particles to tend to clot and string when it was attempted to shower a uniform layer of them on the tissue. Using a rotary brush and coaxial semi-cylindrical screen to produce the layer forming particle shower, acceptable results could be obtained but only at tissue speeds of 200 or less linear feet per minute, substantially lower than was desired for manufacturing cost purposes. Additionally, it was frequently necessary to shut down the process to unblind the screen of clots and strings of the sticky particles. At best, the particle layer did not have as much uniformity as desired, which led to a somewhat irregular extent of bonding.

SUMMARY OF THE INVENTION

The object of this invention is to provide an improvement over the prior process last above described by which a similar but superior product can be produced at much greater speeds, such as more than 300 linear feet per minute, and with less manufacturing difficulty.

In attaining this object, the invention provides a process of making a liquid absorbing laminated structure comprising long lengths of absorptive tissues and an intermediate layer of absorptive particles while the tissues are traveling in the direction of their length, which includes the following steps:

a. a first or base tissue is moistened by transferring to its surface a film of moistening liquid;

b. this moistened surface while traveling and supported substantially horizontally is then showered with dry absorbent particles to form a layer thereof, the absorptive particles being of a nature and quantity to be rendered adhesive by the moistening liquid applied in step a;

c. a second or overlay tissue is superposed over the base tissue and particle layer; and d. the assembly is bonded together by passing it through the nip between a heated roller having a surface temperature of at least 110° C. and a pressure roller, the rollers being pressed together at the nip by a pressure of at least 350 lbs. per square inch and each roller having a surface hardness in excess of 90 Shore A Durometer.

The moistening liquid applied in step a is usually water, as most absorbent particles contemplated are rendered sufficiently adhesive or tacky by absorption of a small amount of water. The amount of liquid applied is generally small, being preferably between 10% and 30%, most preferably about 20%, by weight of the weight of the particle layer applied in step b. To permit uniform, controlled application of such small amounts of liquid, which in many cases is less than a cubic centimeter per square foot of tissue, the liquid is preferably transferred to the tissue from the surface of a transfer roller rotating in the direction opposite to the direction of travel of the tissue.

After step a, the base tissue is preferably drawn onto the surface of the rotating heated roller used in step d with its moistened face outward while the roller surface is moving upwardly toward the top of its path about its axis. The shower of dry absorbent particles of step b is centered on the highest point of the roller path and extends a short distance to either side thereof, so that the base tissue is substantially horizontally disposed while it receives the showered particles. The absorbent particles applied in step b are dry and free-flowing in nature. They are of a nature to be rendered tacky when slightly moistened, a characteristic possessed by most absorbent particles, particularly super-absorbent particles, that are used in making tissue-absorbent particle composites. They are preferably applied in amount between about 2 and 8 grams per square foot of laminate.

To produce the particle shower of step b, the rotary brush and coaxial semi-cylindrical screen used in the prior process of applicant's assignee described above was tried and proved to be unsatisfactory. The dry powder was not applied with the desired uniformity either longitudinally or traversely and could not be accurately controlled to the selected weight of powder.

These difficulties were overcome by constructing a modified application unit in which the ends of the rotary brush shaft were mounted for independent vertical adjustment instead of being mounted in fixed position as they were in the earlier unit, and by replacing the 180° screen of the prior unit with a shroud and screen in which only the central 60° or less is screen and the remainder is closed-walled shroud.

By the first of these changes it became possible to obtain precise alignment of the brush axis with the screen axis needed for uniformity of particle shower transversely of the tissue. Even more importantly, it became possible to adjust the clearance between brush and screen and so to vary the extent to which the brush acts positively as a thrust device as well as a conveying device, to force the particles through the screen. The second of these changes eliminated a high angularity to the horizontal plane of the prior 180° screen towards its opposite sides in the direction of travel of the tissue, which had resulted in an irregular particle shower which was thicker at each side than in the middle. Also, with this change, it became feasible to adjust the brush shaft vertically without significantly differentially changing the clearance between the brush and the screen.

It is preferred therefore that the particle shower be produced by the modified rotating brush type screen just described, which our work has indicated produces a more uniform and precisely controllable particle layer than would be obtainable with oscillating type screens.

In step c the overlay tissue is preferably applied immediately after the particle layer is formed to prevent any tendency of the particles to migrate and bunch before the pressure nip in step d.

In step d, both the heat and pressure applied are important to obtain the desired bonding. Too little heating will not adequately set the tissue-to-particle layer bonds. On the other hand, excessive heating would produce significant vaporization loss of applied moisture and therefore should be avoided. The most desirable surface temperature for the heated roller will depend upon the length of time the moistened base tissue is in contact with it. In the preferred process, the heated roller may have a diameter as small as two feet and the moistened tissue is in contact with it for considerably less than a full revolution. At processing speeds of 300 linear feet per minute or higher the time of contact between any given point on the moistened tissue and the heated roller is of the order of one second. With this short time, the minimum temperature of 110° C. mentioned will not be sufficient in most cases and the roller is preferably heated to 150° C. or higher. With a considerably larger diameter heated roll and/or slower processing speeds, the longer heating periods can make it feasible to heat to lower temperatures. Heating of the moistened tissue before it reaches the pressure nip is believed to have a beneficial effect in driving the moisture toward the overlay tissue.

The pressure applied at the nip and the hardness of the roller surfaces applying it are both crucial. It is desirable to employ an elastomer covered roller as the pressure roller but the elastomer covering should have a hardness in excess of 90 Shore A Durometer, preferably as hard as can be obtained. The larger diameter heated roller may be of steel having greater hardness. The fact that the pressure roller of lesser hardness used in the prior process of applicant's assignee mentioned above did not operate satisfactorily in the present process, indicates that the hardness was not great enough to avoid indenting of the roller by irregularities in thickness of the particle layer encountered, rather than their being crushed flat between the rollers. Pressures of between about 350 and 500 pounds per square inch have been employed to obtain satisfactory bonding, generally better at the higher levels.

The particular tissues used in the process are a matter of choice, bearing in mind that they must have sufficient tensile strength to sustain the tension to which each is put in the process. Since the base tissue is moistened, it needs some wet strength as well as dry strength, even though the tensional stress is kept low. Absorptive tissues of adequate wet strength are available and suitable. A wet strength in the significant longitudinal direction of the order of 600 grams, 3-inch wide strip, is preferred. This provides adequate wet strength margin over normally applied tension with other characteristics being suitable. Estimated maximum longitudinal stress in the preferred process is between 100 and 200 grams per transverse inch.

Since the absorptive particle layer shields the overlay tissue from the moistened base tissue until bonding, the overlay tissue need have no wet strength characteristics, although of course it may have. It is presently preferred to use for the overlay a light tissue, basis weight about 1.6 gm./$f^2$ such as the tissue identified as "Code 290", available from Lincoln Pulp & Paper Company of Lincoln, Me. This tissue has substantially zero wet strength and is not suitable for the base tissue. However, a heavier weight tissue, even if bonded only by fiber entanglement, may have sufficient wet strength to be used as the base tissue.

DESCRIPTION OF THE DRAWINGS

In the accompanying drawings.

DESCRIPTION OF THE PREFERRED EMBODIMENT

Figure 1:
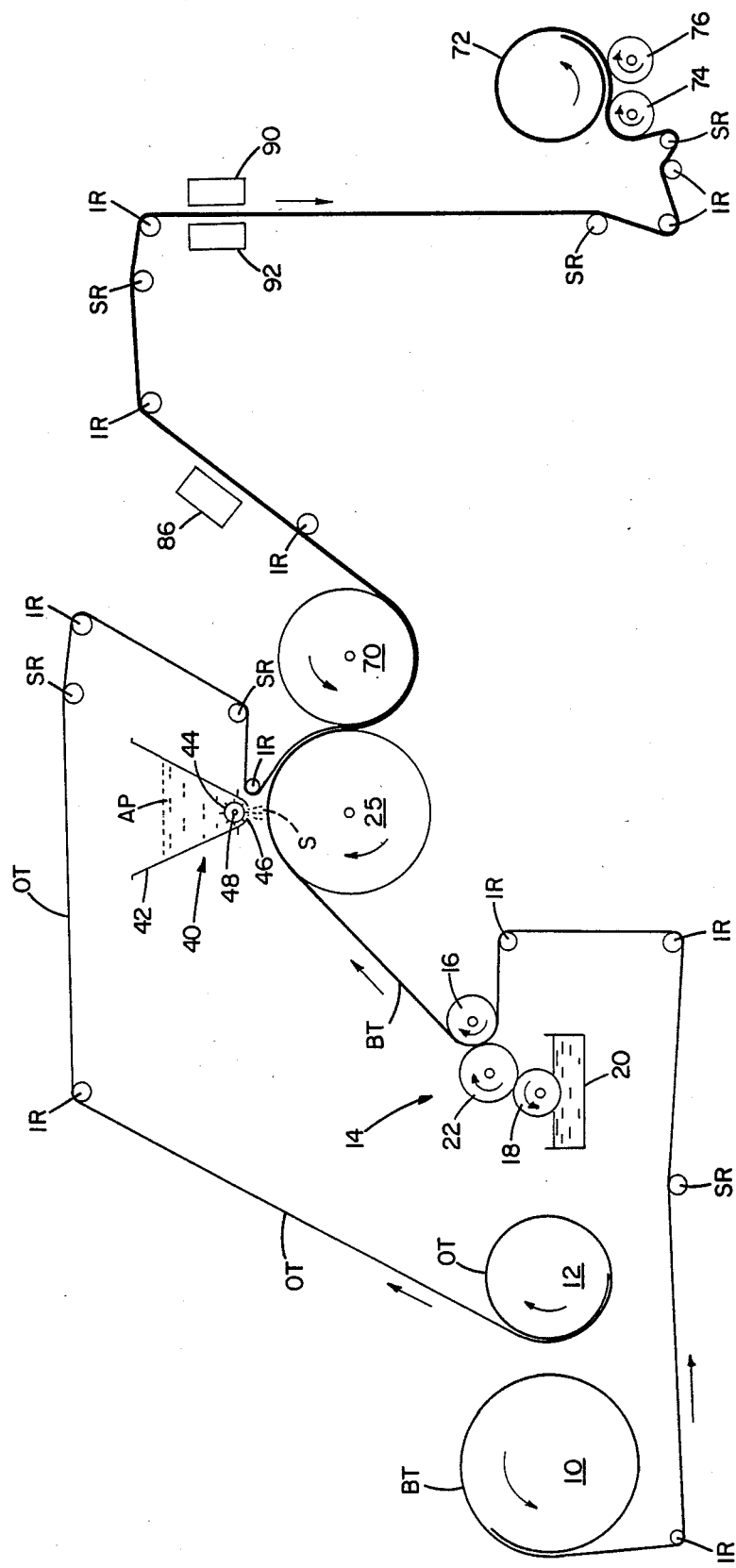
FIG. 1 is a diagrammatic side view.

The apparatus and its organization shown in the drawings are presently used by applicants' assignee, and presently preferred by applicants, for the practice of the process of the invention.

Referring to FIG. 1, a supply roll 10 of the base tissue BT and a supply roll 12 of the overlay tissue OT are mounted on separate unwind stands (not shown) of conventional form having the usual unwind tension control brake, hand-adjustable. This brake is usually set to its approximate minimum. The base tissue is drawn from the supply roll 10 over intermediate idler rollers IR to a moistening unit, generally designated 14, by rotation of the backup roller 16 of the unit in the clockwise direction in the drawing as indicated by the arrow in FIG. 1. The moistening unit shown is a commercially available unit purchased from Dahlgren Manufacturing Company of Dallas, Tex. It has a resilient metering roller 18 which dips in a liquid reservoir 20 and wets the surface of transfer roller 22 which is hydrophilic and is rotated so that its surface is moving in the direction opposite to the surface of the backup roller 16 at the nip between them, as indicated by the arrows.

Figure 2:
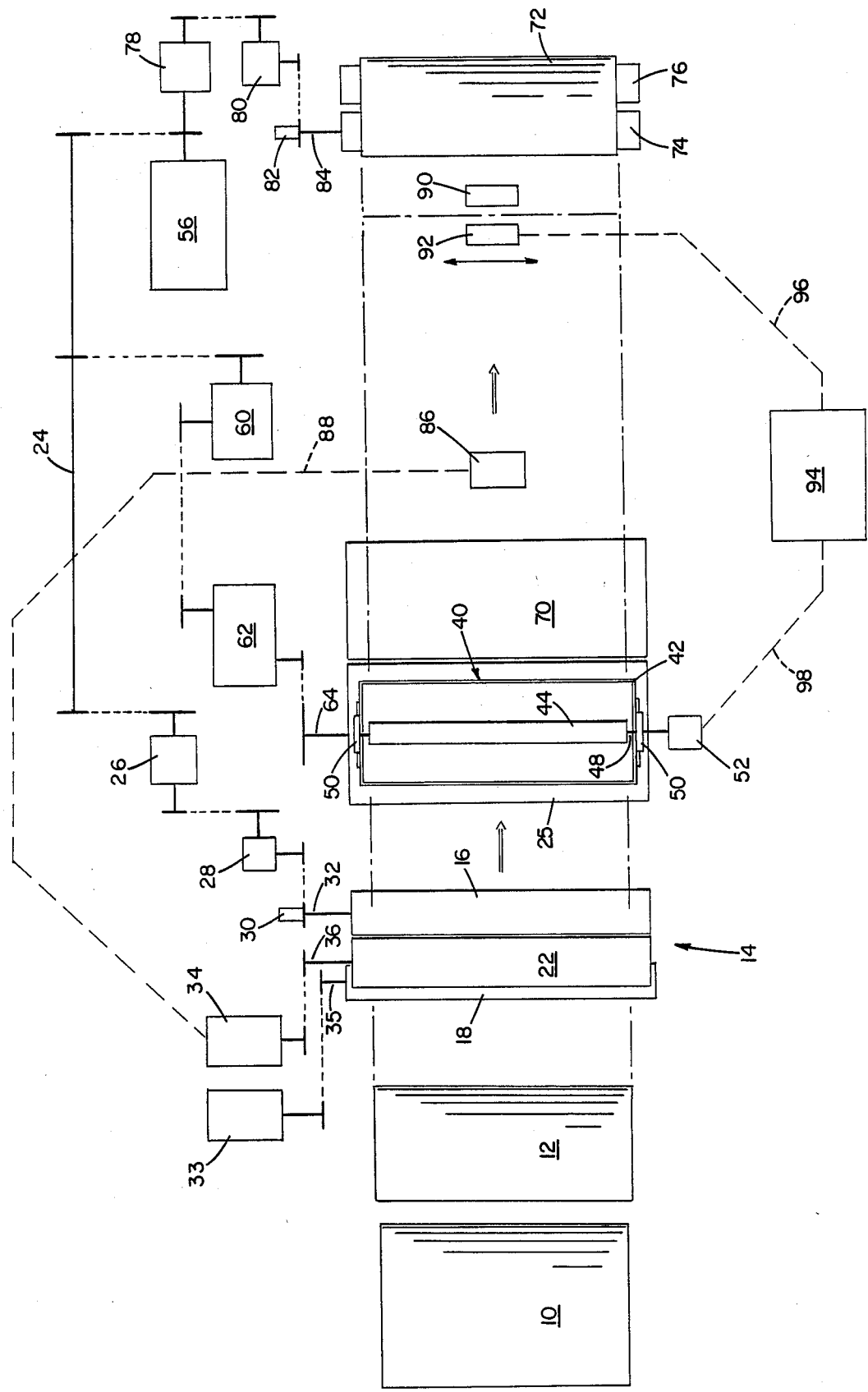
FIG. 2 is a diagrammatic top plan view of the preferred embodiment of apparatus for the practice of the invention.

The backup roller 16 is rotated at a surface speed slightly slower than that of the heated roller 25 to which the base tissue passes after it is moistened by the unit 14, the roller 25 being rotated at the slightly higher surface speed of the laminate in the process. The light tension thus applied to the base tissue is beneficial in keeping it open and flat as it is transferring to heated roller 25. The nip between rollers 16 and 22 of the moistening unit is adjusted to slightly less clearance than the thickness of the base tissue, so that roller 22 just brushes the surface of the base tissue passing through the nip. Desirably, the adjustment permits the base tissue to be pulled through the nip by hand without turning the rollers 22 and 16, although the tissue is in sliding contact with both rollers. Referring to FIG. 2, backup roll 16 is driven from the main drive shaft 24 by connection to speed change gearing 26 and intermediate gearing 28 connected to a manually operated clutch 30 on the shaft 32 of the roller 16. Transfer roller 22 is driven by a variable speed drive motor 34 connected to the roller shaft 36. The transfer roller functions to transfer to the exposed surface of the base tissue BT on the roller 16 at the nip a metered film of liquid applied to the transfer roller by the metering roller 18. The metering roller 18 is driven by a variable speed drive and motor unit 33 connected to its shaft 35. The amount of liquid transferred by the transfer roller 22 to the tissue is controlled by varying the speed of the transfer roller through connection of motor 34 to a moisture meter, as later described.

The base tissue is drawn from roller 16 onto the surface of heated roller 25 by the rotation of that roller clockwise as indicated in FIG. 1 and as it approaches its uppermost position centered over its axis, where the exposed moistened surface of the base tissue BT is showered with dry absorbent particles by an applicator unit designated generally 40. This unit preferably, as shown, has a trough shaped feed hopper 42 mounted to extend across the path of the base tissue and containing a supply of the absorbent particles AP from which a shower S of the particles extending across the base tissue is produced as now described.

Hopper 42 has an open bottom in which is mounted a full bristled rotary brush 44. A shroud and screen member 46 (FIG. 1) of substantially semi-circular cross-section is demountably attached to the bottom of hopper 42 and surrounds the bottom half of brush 44 with close clearance. The screen is located in the central 60° of member 46, the remainder of the member being a closed wall shroud. The opposite ends of shaft 48 of brush 44 are mounted in bearings in blocks 50 (FIG. 2) which are vertically movable in slideways on the opposite ends of hopper 42. Each block 50 has a mechanical jack mechanism (not shown) connected to it for independent vertical adjustment of the ends of shaft 48. The range of adjustment need not be large since normally only small fractions of an inch changes are made. Brush 44 is rotated by a motor and variable speed gearing unit 52 (FIG. 2) which may be mounted for vertical movement with blocks 50 or the motor may be fixedly mounted, with sliding parts provided in the gearing to accommodate the movement of the blocks.

Brush 44 is rotated counterclockwise in FIG. 1 to convey the particles AP from the supply thereof in hopper 42, to which the upper half of the brush is continually exposed, to and through the screen of member 46 to form the shower S. The ends of shaft 44 are adjusted vertically to provide vertical alignment of the brush axis with the screen axis and to provide the desired amount of clearance (if any), between brush and screen. With these adjustments made to suit a particular type and amount of absorbent particles to be applied, control of the shower S to keep the applied particle layer within close limits of the target value is accomplished by varying the speed of rotation of the brush, as hereinafter described.

The screen of member 46 desirably has as much open area as practical, with apertures of a size close to, but sufficient to clear, the largest size particles of the particular absorptive particles being used. When using a preferred superabsorbent particulate material, a sodium acrylate polymer available under the trade designation "Water-Lock" J500 from Grain Processing Corporation of Muscatine, Ia., a preferred screen has a 15×15, 225 holes per square inch construction, with a hole diameter of 0.045 (1.14 mm) and an open area of 37%. The length of the screen in the direction of tissue travel is preferably about two inches, for an angular width of less than 50°, when applying 5 grams or less of the absorbent particles per square foot of the base tissue.

The heated roller 25, which is heated by a circulating electrically heated oil system (not shown), is rotated at a surface speed equal to the processing speed of the laminate by a speed reducer unit 60 (FIG. 2) connected to a variable speed change unit 62 which in turn is connected to the drive shaft 64 of the roller 25. Main drive shaft 24 is driven by connection to a main motor 56.

The overlay tissue OT is withdrawn by rotation of heated roller 25 from supply roll 12, over idler rollers IR and bowed spreader rollers SR, being laid over the particle layer on tissue BT immediately after the layer has been formed thereon. From this point, rotation of the roller 25 carries the assembled laminate to the nip of roller 25 and a slightly smaller diameter pressure roller 70 (as shown, 24 inches and 20 inches, respectively). Pressure roller 70 is rotated by roller 25 (through the intermediate laminate) in the same surface direction, as indicated by the arrows on these respective rollers. In accordance with previous description herein, pressure roller 70 has a steel core with a smooth elastomeric-covering of +90 Shore A Durometer hardness. Currently, the hardness of this rubber surface is 100 Shore A Durometer. Roll 70 is pivotally mounted 0435 for movement toward and away from roller 25 for initial threading purposes, and is hydraulically loaded (by conventional hydraulic pressure equipment not shown) to force it toward roller 25 to provide uniform pressure at the nip between the rollers of 350 pounds per square inch and upwards as far as desired, which includes a presently utilized pressure of about 450 pounds per square inch.

After bonding at the pressure nip, the laminate is driven by the pressure nip and directed by idler rollers IR and bowed spreader rollers SR to be taken up by rewinding into a finished product roll 72. Roll 72 is mounted on a rewind stand of which only rollers 74 and 76 of the same diameter are shown. In this type of rewind stand, a core is placed on the rollers 74, 76 with its axis centered between them. These rollers are rotated in unison in the same direction as indicated by the arrows, which in turn rotates the core, winding the product around it. As the winding proceeds and the wound roll 72 thickens, the core rises correspondingly vertically in guideways provided in the stand. Roller 74 is driven (FIG. 2) from main motor 56 through speed change gearing 78, intermediate gearing 80 and a clutch 82 connecting to the shaft 84 of roller 74. Roller 74 drives roller 76 at the same speed through intermediate connections (not shown). In operation, speed change mechanism 78 is adjusted to rotate roller 74 at a surface speed equal to that of heated roller 25 so that the laminated product is at 0 to slight tension as it is drawn into the nip between the roller 74 and the wound roll 72. It should be noted that since rollers 16, 25 and 74 are driven from the main motor 56, increases or decreases in the speed of this motor will not change the pre-set speed ratios between these rollers, although changing the actual speeds of each of them.

A moisture meter 86 is mounted to scan the laminate as it travels away from the nip of rollers 25 and 70. The particular meter used is of the infra-red type and was purchased from Moisture Systems, Inc. of Hopkinton, Mass. Meters for the same purpose of the same or other type are available from various suppliers and may be used. Meter 86 is electrically connected to the variable speed motor 34 which drives transfer roller 22 of the moistening unit, as indicated by the dashed line 88 in FIG. 2. The meter is set to have a first electrical output if the moisture reading exceeds the target value by a predetermined amount, and a second electrical output if the reading is a predetermined amount less than the target value. These two outputs are translated at motor 34 into opposite changes in the speed of rotation of transfer roller 22.

Motor 34 is initially adjusted to provide an estimated proper surface speed for roller 22, this normally being about 100 feet per minute or more above the surface speed of the base tissue in the opposite direction. An electrical signal from meter 86 indicating too much moisture causes the speed of rotation of roller 22 to be reduced, reducing the amount of liquid applied to the base tissue, while a signal indicating too little moisture has the opposite effects. In this way the applied moisture is readily kept within ±10% of the target amount.

Since the moisture meter 86 is in position only to scan the product after it leaves the pressure nip, its readings do not precisely reflect the amount of moisture added. Instead, its readings give moisture applied less moisture loss up to the point of scanning. This is desirable, since if there is moisture loss above or below a normal minor amount, this too should be corrected by adding more or less moisture, respectively. The readings of the meter in its present location are considered sufficiently representative of the amount of applied moisture to make it unnecessary to provide a second meter scanning the base tissue as it passes from the moistener unit to the heated roller 25. The nul range of the meter 86 is thus adjusted to the target moisture content of the finished product rather than directly to applied moisture.

Beyond the meter 86 the product passes between the source unit 90 and the detector unit 92 of what is generally known as a "Beta-Gage", though other devices which are similarly effective may be used. The particular Beta-Gage used was purchased from Indev Corporation of East Providence, R.I.

In the Beta-Gage device, the source unit 90 emits energy rays from a source material such as promethium through the laminate to the detector unit 92, which reports detection to a computer 94 (FIG. 2) to which it has electrical connections indicated by dashed line 96 in FIG. 2. The computer correlates transmission and reception to provide weight readings such as in grams per unit area. Computer 94 can be programmed to provide electric output signals, transmitted by connected wiring indicated by dashed line 98 in FIG. 2, to actuate the speed change gearing of motor and gearing unit 52, altering the speed of rotation of the rotary brush 44 of the absorbent particle applicator 40, which is normally rotated at a speed between 2 and 4 r.p.m. A signal indicating too much weight slows the rotation of the brush to decrease the amount of absorptive particles in the shower S while a signal indicating too little weight has the opposite effects.

With the moisture content of the finished laminate closely controlled as indicated, the absorptive particle applicator is the only significant potential source of variation in product weight. Using the Beta-Gage control applicator unit 40 along with the moisture meter control of the moistening unit 14, we have been consistently able to maintain finished product weight in grams per square foot within $\pm \frac{1}{2}$ gram of target weight at all speeds utilized.

Automatic splicers and reloaders could be provided for replacing spent tissue supply rolls 10 and 12 but this has not been deemed economically justified up to the present. The tissue rolls used are available in lengths of 20,000 feet or more. Shut down, manual splicing and roll replacement take about 5 to 10 minutes. Similarly, the product roll 72 is manually removed and a new core substituted. Equipment for automating this operation also is available if desired.

In shutting down the process, the absorbent powder applicator unit is stopped by stopping brush motor 52, almost simultaneously with but slightly before, moving the backup roller 16 of the moistening unit 14 away from its transfer roller 22 to stop the moistening, then main motor 56 is shut down. The objective here is to prevent moistened base tissue without a layer of absorptive particles reaching the overlay tissue before the main motor is shut off, since this could wet the overlay tissue sufficiently to cause it to break if, as may often be the case, the overlay tissue has substantially zero wet strength. Upon shutting off the main motor, the pressure roller 70 is backed off the heated roller 25, opening the pressure nip, and the Beta-Gage is taken off-line.

In re-starting the process, the pressure roller is returned to pressure nip position, the main motor 56 is started and gradually brought up to final operating speed, and the Beta-Gage is put on-line. Almost simultaneously, backup roller 16 is brought back to moistening position and brush motor 52 is turned on, but this time with moistening restored slightly before powder feeding.

We claim:

1. A process of making a liquid absorbing laminated structure comprising long lengths of absorptive tissues and an intermediate layer of absorptive particles while said tissues are traveling in the direction of their lengths which comprises the steps of:
  a. applying a moistening liquid substantially uniformly to a first of said tissues by transferring a film of moistening liquid to a surface of said tissue;
  b. showering said surface of said first tissue while substantially horizontally supported with dry absorbent particles to form a layer of said particles thereon, said absorptive particles being of a nature and quantity to be rendered adhesive by absorption of the moistening liquid applied in step a;
  c. superposing a second of said tissues on said first tissue and particle layer thereon; and
  d. bonding together the tissue particle assembly by passing it through the nip between a heated roller having a surface temperature of at least 110° C. and a pressure roller, said rollers pressed together at the nip by a pressure of at least 350 pounds per square inch and each having a surface hardness in excess of 90 Shore A Durometer.

2. A process according to claim 1 wherein the transfer of moistening liquid film in step a. and the amount of the absorptive particles showered in step b. are regulated so that the weight of moisture transferred in step a. is substantially constant and between 10% and 30% of the weight of the absorptive particle layer formed in step b.

3. A process according to claim 2 wherein the weight of moisture transferred in step a. is about 20% of the weight of the absorptive particle layer formed in step b.

4. A process according to claim 2 wherein the weight of the particle layer formed in step b. is maintained at a substantially constant value of between 2 and 8 grams per square foot of the laminate.

5. A process according to claim 1, wherein the particle shower of step b. is produced by rotating a supply of said particles about an axis above, parallel to, and transverse to the path of travel of, said first tissue, and separating said supply into falling particle streams of approximately the cross-section size of the largest particles in said supply, while said supply is moving through an arc about said axis of less than 60° having its transverse center line in vertical alignment with said axis.

6. A process according to claim 1 wherein said opposed pressure applied in step d. is at least about 450 pounds per square inch.

7. A process according to any of claims 2 to 6 wherein said tissues are traveling at least at 300 feet per minute, the outer surface of said first tissue is heated to at least 150° C. during steps b., c., and d., and step c. immediately follows step b.

* * * * *

UNITED STATES PATENT AND TRADEMARK OFFICE
CERTIFICATE OF CORRECTION

PATENT NO. : 4,851,069

DATED : July 25, 1989

INVENTOR(S) : Thomas D. Packard et al.

It is certified that error appears in the above-identified patent and that said Letters Patent is hereby corrected as shown below:

TITLE PAGE:
Change "[73] Assignee: Bird Machine Company, Inc., South Walpole, Mass." to
--[73] Assignee: Micrex Corporation, Walpole, Mass.--

Column 6, line 60, delete "0435".

Signed and Sealed this

Twenty-first Day of May, 1991

Attest:

HARRY F. MANBECK, JR.

Attesting Officer

Commissioner of Patents and Trademarks